United States Patent
Sura et al.

(10) Patent No.: US 10,632,043 B2
(45) Date of Patent: Apr. 28, 2020

(54) PREMIX FORMULATION FOR PARENTERAL USE AND PACKAGING THEREOF

(71) Applicants: Siva Prasad Reddy Sura, Hyderabad (IN); Surya Kumari Padala, Hyderabad (IN); Vikas Chandel, Hyderabad (IN); Arvind Gannimitta, Hyderabad (IN); Jayant Karajgi, Hyderabad (IN); Sivakumaran Meenakshisunderam, Hyderabad (IN)

(72) Inventors: Siva Prasad Reddy Sura, Hyderabad (IN); Surya Kumari Padala, Hyderabad (IN); Vikas Chandel, Hyderabad (IN); Arvind Gannimitta, Hyderabad (IN); Jayant Karajgi, Hyderabad (IN); Sivakumaran Meenakshisunderam, Hyderabad (IN)

(73) Assignee: Aurobindo Pharma Ltd, Hyderabad (IN)

( * ) Notice: Subject to any disclaimer, the term of this patent is extended or adjusted under 35 U.S.C. 154(b) by 0 days.

(21) Appl. No.: 16/285,527

(22) Filed: Feb. 26, 2019

(65) Prior Publication Data

US 2019/0183729 A1 Jun. 20, 2019

Related U.S. Application Data

(63) Continuation-in-part of application No. 15/348,374, filed on Nov. 10, 2016, now abandoned.

(30) Foreign Application Priority Data

Nov. 11, 2015 (IN) .......................... 6090/CHE/2015

(51) Int. Cl.
| | | |
|---|---|---|
| *A61K 31/415* | (2006.01) | |
| *A61K 9/00* | (2006.01) | |
| *A61J 1/14* | (2006.01) | |
| *A61J 1/10* | (2006.01) | |
| *B65B 55/02* | (2006.01) | |
| *A61K 47/02* | (2006.01) | |
| *B65B 3/00* | (2006.01) | |
| *A61K 31/4174* | (2006.01) | |
| *A61J 3/00* | (2006.01) | |
| *B32B 1/00* | (2006.01) | |

(52) U.S. Cl.
CPC .............. *A61J 1/1468* (2015.05); *A61J 1/10* (2013.01); *A61J 1/1406* (2013.01); *A61J 1/1475* (2013.01); *A61J 3/002* (2013.01); *A61K 9/00* (2013.01); *A61K 31/4174* (2013.01); *A61K 47/02* (2013.01); *B32B 1/00* (2013.01); *B65B 3/003* (2013.01); *B65B 55/027* (2013.01)

(58) Field of Classification Search
CPC .................................................... A61K 31/4164
USPC .......................................... 514/396; 424/400
See application file for complete search history.

(56) References Cited

U.S. PATENT DOCUMENTS 8,338,470 B1 * 12/2012 Roychowdhury .......................... A61K 31/4174
514/396
8,829,054 B1 * 9/2014 Owoo ....................... A61J 1/00
514/652

OTHER PUBLICATIONS

Anderson et al. "Stability of dexmedetomidine 4 ug/mL in polypropylene syringes," Am. J. Health-Syst Pharm. 2012, vol. 69, pp. 595-597 (Year: 2012).*
Sealed Air Nexcel M312, M312A, M312C. http://www.sealedairmedical.com/ap/en/Nexcel_Pharma/M312-312A-312C.aspx (Year: 2013).*

* cited by examiner

*Primary Examiner* — Shengjun Wang
(74) *Attorney, Agent, or Firm* — Jay R Akhave

(57) ABSTRACT

The present invention relates to stable premix formulations for parenteral use and packaging for such formulations. The present invention relates to use of a single layer or multilayer film bags comprising polypropylene for packing premixed injectable formulations which remain stable during the storage period.

The present invention relates to use of a single layer or multilayer film bags comprising polypropylene for packing dexmedetomidine premixed formulations. Such stable premixed formulations packed into a single layer or multilayer film bags comprising polypropylene are highly advantageous since they are ready-to-use, for example, in perioperative care of a subject in need thereof for sedation.

9 Claims, No Drawings

PREMIX FORMULATION FOR PARENTERAL USE AND PACKAGING THEREOF

CROSS REFERENCE TO RELATED APPLICATIONS

This application claims priority from an Indian Patent Application IN 6090/CHE/2015 filed on Nov. 11, 2015 and is a continuation-in-part of U.S. Ser. No. 15/348,374 filed on Nov. 10, 2016

FIELD OF THE INVENTION

The present invention relates to stable premix formulations for parenteral use and packaging for such formulations. The present invention relates to use of a single layer or multilayer film bags comprising polypropylene homopolymer for packing premixed injectable formulations which remain stable during the storage period.

The present invention relates to use of a single layer or multilayer film bags comprising polypropylene homopolymer for packing dexmedetomidine premixed formulations. Such premixed formulations packed into a single layer or multilayer film bags comprising polypropylene homopolymer are highly advantageous since they are ready-to-use, for example, in perioperative care of a subject in need thereof for sedation.

The present invention also relates to use of a single layer or multilayer polypropylene homopolymer film bags for packing stable premixed formulations comprising dexmedetomidine or a pharmaceutically acceptable salt thereof, that can be used for sedating initially intubated and mechanically ventilated patients during treatment in an intensive care setting, and for sedating of non-intubated patients prior to and/or during surgical and other procedures.

BACKGROUND OF THE INVENTION

With a share of approximately 27% having value of S860-billion dollar, injectables were No. 2 in the drug delivery market in 2010, preceded only by oral medication. Double-digit growth rates, mainly triggered by biotech-derived products and the rise of injectable generics show that the importance of this segment is still on the rise. Still, prefillable glass syringes and vials are the most common primary packaging containers for modern injectables. Various glass container systems are traditionally used for the storage of parenterals. However, the container of a product intended for parenteral use has to ensure that functionality and drug delivery accuracy and always comply with the specifications throughout the product shelf life. Several factors have to be considered when choosing the right packaging/container for an injectable product, such as drug product formulation properties, dosage, type of application, stability, storage condition and duration, and end-user friendliness. It may be necessary to develop different packaging systems for one product to satisfy different patient group needs.

A dominant trend in primary packaging is the evolution from simple bulk packaging materials toward ready-to-sterilize (RTS) or ready-to-use (RTU) primary packaging components and systems. Further, the Regulatory authorities all over the world are paying greater attention to the use of appropriate primary packaging materials with the consequence that standards have become very comprehensive and detailed. Quality requirements for glass containers, which are likely to be tightened up, include specifications regarding the particle load, lower rates of cracks or cosmetic defects, and smaller dimensional tolerances. Available container closure systems/devices include vials, reconstitution kits, disposable or prefillable syringes, ampoules and auto injectors or pen systems. Although plastic materials are also being considered for use as primarily packing materials particularly for infusions for parenteral use; the challenge has been to develop packaging which are compatible with the contents, minimizes extractables/leachables, are solvent-resistant, and durable.

Racemic 4-[1-(2, 3-dimethylphenyl) ethyl]-1H-imidazole, which is known under the name medetomidine, is a selective and potent $\alpha_2$-adrenoceptor agonist. Medetomidine has been used as an antihypertensive agent and as a sedative-analgesic agent. It has further been observed that this compound also possesses anxiolytic effects and can therefore be used in the treatment of general anxiety, panic disorder and various types of withdrawal symptoms.

The d-enantiomer of medetomidine, the generic name of which is dexmedetomidine, is described in U.S. Pat. No. 4,910,214 as an $\alpha_2$-adrenoceptor agonist for general sedation/analgesia and the treatment of hypertension or anxiety. U.S. Pat. Nos. 5,344,840 and 5,091,402 discuss dexmedetomidine in perioperative and epidural use, respectively. For example, when used in perioperative care, dexmedetomidine can reduce the amount of anesthetic necessary to anesthetize a patient. Additionally, U.S. Pat. No. 5,304,569 discusses the use of dexmedetomidine in treating glaucoma, and U.S. Pat. No. 5,712,301 discusses the use of dexmedetomidine for preventing neurodegeneration caused by ethanol consumption. Furthermore, U.S. Pat. No. 6,716,867 discloses methods of sedating a patient while in an intensive care unit by administering dexmedetomidine, or a pharmaceutically acceptable salt thereof, to the patient.

Precedex™ (dexmedetomidine hydrochloride) injection is a sterile, nonpyrogenic solution suitable for intravenous infusion following dilution. Precedex (dexmedetomidine hydrochloride) in 0.9% Sodium Chloride Injection is a sterile, nonpyrogenic ready-to-use solution suitable for intravenous infusion. Dexmedetomidine hydrochloride is the S-enantiomer of medetomidine and is chemically described as (+)-4-(S)-[1-(2, 3-dimethylphenyl) ethyl]-1H-imidazole monohydrochloride.

Precedex™ in 0.9% Sodium Chloride Injection is supplied as a clear, colorless, isotonic solution with a pH of 4.5 to 8.0. Precedex™ (dexmedetomidine hydrochloride in 0.9% Sodium Chloride) injection is available as 80 mcg/20 mL (4 mcg/mL), 200 mcg/50 mL (4 mcg/mL) and 400 mcg/100 mL (4 mcg/mL) in 20 mL clear glass vials, 50 mL and 100 mL clear glass bottles, respectively. Containers are intended for single use only. Each ml contains 4.72 mcg of dexmedetomidine hydrochloride equivalent to 4 mcg (0.004 mg) of dexmedetomidine and 9 mg sodium chloride in water. The solution is preservative-free and contains no additives or chemical stabilizers.

Precedex™ is indicated for sedating initially intubated and mechanically ventilated patients during treatment in an intensive care setting and for sedation of non-intubated patients prior to and/or during surgical and other procedures. Precedex™ should be administered by continuous infusion not to exceed 24 hours. Precedex™ has been continuously infused in mechanically ventilated patients prior to extubation, during extubation, and post-extubation.

Patients in intensive care unit (ICU) are treated with many interventions most notably endotracheal intubation and mechanical ventilation that are observed to be distressing.

Pain is the most common in intensive care unit (ICU) patients. Sedation is commonly used in the intensive care unit (ICU) to reduce patient discomfort, improve tolerance with mechanical ventilation and reduce metabolic demands during respiratory and hemodynamic instability. Continuous and deep sedation have been associated with increased risk of delirium, longer duration of mechanical ventilation, increased length of ICU and hospital stays, and long-term risk of neurocognitive impairment, post-traumatic stress disorder, and mortality. Sedation interruption and protocolized sedation have been associated with decreased length of ICU stay and reduced duration of mechanical ventilation.

Sedation has been achieved with clonidine, midazolam or propofol in intensive care units (ICUs). Dexmedetomidine is a more potent a-agonist; it is showing promise as a sedative agent in ICU and in pediatric anesthesia due to its shorter elimination half-life. Dexmedetomidine, an $\alpha_2$-agonist available for ICU sedation, may reduce the duration of mechanical ventilation and enhance patient comfort. Use of dexmedetomidine may have an advantage in maintaining lighter levels of sedation during early sedation, which is associated with improved clinical outcomes.

U.S. Pat. Nos. 8,242,158; 8,338,470; 8,436,033; 8,455,527 and 8,648,106 disclose ready-to-use liquid pharmaceutical composition for parenteral administration to a subject, comprising dexmedetomidine or a pharmaceutically acceptable salt thereof at a concentration of about 4 µg/mL disposed within a sealed glass container.

U.S. Pat. No. 8,242,158 provides a ready-to-use liquid pharmaceutical composition comprising dexmedetomidine or a pharmaceutically acceptable salt thereof at a concentration of about 4 µg/mL disposed within a sealed glass container. U.S. Pat. No. 8,242,158 also discloses studies for selection of packaging components for premixed dexmedetomidine pharmaceutical composition. In order to identify suitable primary packaging components for the 4 µg/mL premixed dexmedetomidine composition in 0.9% NaCl, stability studies were conducted in various configurations including glass vials, ampoules, plastic flexible containers (CR3 elastomer copolyester ether containers (Hospira, Inc., Lake Forest, Ill.), PVC and VisIV™ plastic containers (Hospira, Inc., Lake Forest, Ill.)), and Ansyr® syringes (Hospira, Inc., Lake Forest, Ill.). The samples of 4 µg/mL premixed dexmedetomidine composition in 0.9% NaCl, with pH of 4.7-6.2, were packed in aforementioned packs and autoclaved. The stability of the autoclaved samples were tested under accelerated conditions (40° C./75% RH) and evaluated over a period of 5 months. After five months under accelerated conditions the potency of the premixed dexmedetomidine composition in glass ampoules and vials remained at about 98% while that in the syringe was found to be about 90%. In PVC and CR3 elastomer copolyester ether bags (Hospira, Inc., Lake Forest, Ill.), after the initial potency loss to around 80% no further loss of potency was observed during the five month period. The cause of potency loss in PVC bags and CR3 elastomer copolyester ether bags (Hospira, Inc., Lake Forest, Ill.) during autoclaving was investigated. Related substances testing on autoclaved premixed dexmedetomidine composition filled in PVC and CR3 elastomer copolyester ether bags (Hospira, Inc., Lake Forest, Ill.) revealed that potency drop did not occur due to degradation, because the total percent of impurities was much less than 20%. Loss of potency may be due to either adsorption (restricted to the surface of the flex bag) and/or absorption (not restricted to the surface) of the drug in to the flex bags. To confirm the absorption/adsorption phenomena, the CR3 elastomer copolyester ether bags and PVC bags that showed 20% potency loss were emptied and rinsed with methanol. The rinse solvent was tested for dexmedetomidine. Nearly all the drug was recovered from CR3 elastomer copolyester ether bags indicating adsorption and only 1% of the drug was recovered from PVC bags indicating absorption.

The related substances results indicated that premixed dexmedetomidine composition in VisIV™ plastic bags (Hospira, Inc., Lake Forest, Ill.) had high impurity levels higher than levels observed in ampoules, vials, syringes, PVC bags and CR3 elastomer copolyester ether bags (Hospira, Inc., Lake Forest, Ill.).

U.S. Pat. Nos. 8,324,260; 8,507,542; US 2013/0096170; US 2013/0096172 and US 2014/0005243 disclose method of sedation or analgesia in a pediatric patient in need thereof, wherein the method comprises administering dexmedetomidine to the pediatric patient; wherein the dexmedetomidine is administered as a first loading dose at a concentration of about 0.005 to about 0.25 µg/kg prior to a second maintenance dose at a concentration of about 0.005 to about 0.2 µg/kg/hr; wherein the pediatric patient is about one month to about 17 years of age; and wherein the dexmedetomidine is administered as a continuous infusion for a time period of less than about 36 hours.

The aforementioned prior art disclose that all types of Non-Glass containers like PVC bags, CR3 elastomer copolyester ether bags and ADDVantage® PVC bags, are not suitable for premix compositions of dexmedetomidine composition due to loss of drug potency either by adsorption and/or absorption phenomena.

Anderson et al., (Am J health-Syst Pharm—Vol 69, Apr. 1, 2012) discloses that the dexmedetomidine diluted to 4 mg/mL in 0.9% sodium chloride injection was stable for only 48 hours at 20-25° C. and 14 days at 5° C. when stored in polypropylene (PP) syringes. The samples of diluted dexmedetomidine stored in syringes at room temperature exhibited a loss of drug concentration of <10% over 48 hours; the refrigerated samples exhibited a loss of drug concentration of <5% over 14 days. The assay results of Anderson et al in PP syringe conclude that premix compositions of dexmedetomidine were susceptible to loss of drug potency of about 5% over 48 hours. Therefore, Polypropylene was not considered to be an appropriate Material of Construction (MOC) to be suitable as multilayered plastic bags for packing premix compositions of dexmedetomidine.

U.S. Pat. Nos. 9,649,296 and 9,717,796 disclose a premixed ready-to-use for parenteral administration to a subject, comprising dexmedetomidine or a pharmaceutically acceptable salt thereof at a concentration of about 0.5 µg/mL to about 20 µg/mL and a sugar disposed in a flexible plastic container substantially free of DEHP.

Further, the use of glass containers for administering premix compositions particularly as infusion are highly troublesome and dangerous due to the brittle nature of glass and its tendency to break, which renders it highly unsafe particularly for use in intensive care unit (ICU) patients.

Thus the present invention can be said to solve the long felt need for containers/packaging for premixed compositions for parenteral use which are user-friendly, safe, flexible, easy to transport and store, compatible with the contents, minimizes extractables/leachables, solvent-resistant, and durable. The present invention alleviates the limitations in the art by providing such containers/packaging for injectable preparations.

SUMMARY OF INVENTION

Aspects of the present invention relate to stable premix formulations for parenteral use and packaging for such formulations.

Aspects of the present invention relate to use of a single layer or multilayer film bags comprising polypropylene for packing premix injectable formulations which remain stable during the storage period.

Aspects of the present invention also relate to use of a single layer or multilayer film bags comprising polypropylene homopolymer for packing dexmedetomidine premix formulations.

Aspects of the present invention relate to ready-to-use stable premix formulations packed into single layer or multilayer film bags comprising polypropylene homopolymer, and wherein the said bags are sealed.

Aspects of the present invention relate to stable premix dexmedetomidine composition disposed in multilayered bags made from material comprising polypropylene homopolymer.

Aspects of the present invention relate to stable premix dexmedetomidine composition disposed in three-layered or five-layered bags made from material comprising polypropylene homopolymer.

Aspects of the present invention relate to packaging bags comprising at least one injection port, at least one tube port and at least one twist off port.

Aspects of the present invention relate to a single layer or multilayer polypropylene homopolymer film bags for packing stable premix formulations comprising dexmedetomidine or a pharmaceutically acceptable salt thereof, for use in sedating initially intubated and mechanically ventilated patients during treatment in an intensive care setting, and in sedating of non-intubated patients prior to and/or during surgical and other procedures.

Aspects of the present invention provides containers/packaging in the form of sealed bags for stable premixed compositions for parenteral use which are user-friendly, safe, flexible, easy to transport and store, are compatible with the contents, minimizes extractables/leachables, are solvent-resistant, and are highly durable.

DETAILED DESCRIPTION OF THE INVENTION

According to the present invention, premix formulations or premixed formulations or premix compositions or premixed compositions refers to a ready-to-use solution for parenteral use such as infusion which does not require any prior reconstitution or dilution or mixing before administration.

The terms "premix" or "premixed" or "premixture" as used herein refers to a pharmaceutical formulation that does not require reconstitution or dilution prior to administration to a patient. For example, in contrast to non-premix formulations of dexmedetomidine, the premix formulations provided herein are suitable for administration to a patient without dilution.

In the specification, singular forms, including the singular forms "a" "an" and "the", specifically also encompass the plural referents of the terms to which they refer unless the context clearly dictates otherwise. In addition, as used herein, unless specifically indicated otherwise, the word "or" is used in the "inclusive" sense of "and/or" and not the "exclusive" sense of "either/or".

As used in this specification, whether in a transitional phrase or in the body of a claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

The term "formulation" and "composition" used interchangeably unless the context clearly dictates otherwise and refers to liquid having solid particles dissolved or dispersed in a pharmaceutically acceptable solvent or carrier system with or without additional excipients.

The term "pharmaceutically acceptable," when used in connection with the pharmaceutical compositions of the invention, refers to molecular entities and compositions that are physiologically tolerable and do not typically produce untoward reactions when administered to a human Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, dispersing agent or vehicle with which the compound is administered. Such pharmaceutical carriers can be sterile liquids, such as water and oils. For example, water, aqueous solutions, saline solutions, aqueous dextrose or glycerol solutions can be employed as carriers, particularly for injectable solutions. Suitable pharmaceutical carriers are described in, for example, "Remington's Pharmaceutical Sciences" by Philip P. Gerbino, 21st Edition (or previous editions).

According to the invention, a "subject" or "patient" is a human, a non-human mammal or a non-human animal. Although the animal subject is preferably a human, the compounds and compositions of the invention have application in veterinary medicine as well, e.g., for the treatment of domesticated species such as canine, feline, and various other pets; farm animal species such as bovine, equine, ovine, caprine, porcine, etc.; wild animals, e.g., in the wild or in a zoological garden; and avian species, such as chickens, turkeys, quail, songbirds, etc.

The term "stable" as used herein refers to a premix composition and/or a pharmaceutical formulation that retains its physical stability when stored at 40° C./25% RH for 6 months or 25° C./40% RH for 12 months. The term "stable" as used herein also refers to a premix composition and/or a pharmaceutical formulation that retains its physical stability and chemical stability [i.e. Assay & RS (Related substances/impurities)] when stored at stored at 40° C./25% RH for 6 months or 25° C./40% RH for 12 months.

The term "storage period" as used herein refers to a time period during which premix dexmedetomidine composition remains stable when stored at 25° C./40% RH for at least 12 months.

The term "pack" as used herein is referred to primary packaging components, especially the bags/containers which are in direct contact with the premix compositions and/or pharmaceutical formulations of the present invention. For example these packs are made of polypropylene film having single or multiple layers. The multiple layers may be made up of at least three layers of co-extruded Polypropylene films. Usually these multilayers are made up of one or more non-sealant layer and one or more sealant layer composed of Polypropylene homopolymer, SEBS (styrene-ethylene-butadiene block copolymers) and calcium stearate.

The term "about" or "approximately" as used herein means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

In embodiments, the present invention provides stable premix formulations for parenteral use and packaging for such formulations.

In embodiments, the present invention provides a single layer or multilayer film bags comprising polypropylene homopolymer for packing premix injectable formulations which remain stable during the storage period.

In embodiments, the present invention provides a single layer or multilayer film bags comprising polypropylene homopolymer for packing dexmedetomidine premix formulations.

In embodiments, the present invention provides ready-to-use premix formulations packed into a single layer or multilayer film bags comprising polypropylene homopolymer, and wherein the said bags are sealed.

In embodiments, the present invention provides ready-to-use premix formulations packed into multilayer film bags comprising polypropylene, and wherein multilayer film bag is made up of one or more non-sealant layer and one or more sealant layer. The non-sealant and sealant layers are composed of polypropylene homopolymer, SEBS (styrene-ethylene-butadiene block copolymers) and calcium stearate.

In embodiments, the present invention provides stable premix dexmedetomidine composition disposed in multilayered bags made from material comprising polypropylene homopolymer.

In embodiments, the present invention provides stable premix dexmedetomidine composition disposed in three-layered or five-layered bags made from material comprising polypropylene homopolymer.

In embodiments, the present invention provides container/packaging bags comprising at least one injection port, at least one tube port and at least one twist off port. In embodiments, the bags contain injection port which is made up of latex free isoprene rubber closure and polycarbonate body. In embodiments, the bags contain multilayer polypropylene tube port and modified polypropylene twist off port.

In embodiments, the present invention provides a single layer or multilayer polypropylene homopolymer film bags for packing premix formulations comprising dexmedetomidine or a pharmaceutically acceptable salt thereof, for use in sedating initially intubated and mechanically ventilated patients during treatment in an intensive care setting, and in sedating of non-intubated patients prior to and/or during surgical and other procedures.

In embodiments of the present invention, the containers/packaging in the form of sealed bags for premixed compositions for parenteral use according to the present invention are user-friendly, safe, flexible, easy to transport and store, are solvent-resistant, and are highly durable.

In embodiments of the present invention, the material used to make the containers/packaging in the form of bags has improved compatibility with drugs and minimizes extractables/leachables. Further they are transparent, durable, and solvent-resistant. They have a high break-resistance, broader pH range tolerance, and no leakage of metal ions. Further the packaging of the present invention has excellent drainability, which limits the need for excess overfill. Further they have a desirable gas and water vapor permeability.

In embodiments of the present invention, the container/packaging is amenable to known methods of sterilization such as autoclaving. Further, the potency of the active agent contained in the packaging is preserved during sterilization and during storage.

In certain embodiments, the stable premix composition is disposed within a sealed container/packaging which comprises multilayer polypropylene homopolymer coextruded film.

In certain non-limiting embodiments, the multilayered polypropylene homopolymer containers contain premix dexmedetomidine composition at a concentration of about 0.05 µg/ml to about 15 µg/ml, preferably about 1 µg/ml to about 10 µg/ml.

In certain embodiments, the multilayered polypropylene homopolymer containers contain premix dexmedetomidine formulation as a total volume of about 10 mL to about 200 mL, preferably about 15 mL to about 150 mL, most preferably 20 mL, 50 mL or 100 mL.

In certain non-limiting embodiments, the dexmedetomidine compositions of the present invention can be administered as an anxiolytic analgesic to a patient. In certain embodiments, the composition can be administered as a premedication prior to an operation with or without administration of an amount of an anesthetic effective to achieve a desired level of local or general anesthesia.

In certain non-limiting embodiments, the dexmedetomidine compositions of the present invention can be administered as a sedative. In certain embodiments, the composition is administered preoperatively to potentiate the effect of an anesthetic, wherein administration of the composition reduces the amount of anesthetic required to achieve a desired level of anesthesia.

In certain embodiments of the present invention, the stable premixed dexmedetomidine composition is administered parenterally such as, intravenously, intramuscularly, intraperitonealy, subcutaneously, or via an implantable pump.

In embodiments, the stable premix compositions of the invention may be formulated by admixture with a pharmaceutically acceptable carrier or excipient. In certain non-limiting embodiments, the premix compositions are provided in a therapeutically effective amount to an animal, such as a mammal, preferably a human, in need of treatment therewith for inducing a sedative, anxiolytic, analgesic, or anesthetic effect.

In certain non-limiting embodiments, dexmedetomidine is formulated as a composition, wherein the dexmedetomidine is the only therapeutically active ingredient present in the composition. In other non-limiting embodiments, dexmedetomidine is formulated as a composition, wherein the dexmedetomidine is formulated in combination with at least one or more other therapeutically active ingredient. The formulation is preferably suitable for parenteral administration.

In embodiments, the stable premix formulations suitable for injectable use, such as, for example, intravenous, subcutaneous, intramuscular and intraperitoneal administration, include sterile aqueous solutions or dispersions and sterile powders for the extemporaneous preparation of sterile injectable solutions or dispersion. In all cases, the form can be sterile and can be fluid to the extent that easy syringeability exists. It can be stable under the conditions of manufacture and storage and can be preserved against the contaminating action of microorganisms such as bacteria and fungi. The carrier can be a solvent or dispersion medium containing, for example, water, saline, ethanol, polyol (for example, glycerol, propylene glycol, and polyethylene glycol, and the like), suitable mixtures thereof, and oils. The proper fluidity can be maintained, for example, by the use of a coating such as lecithin, by the maintenance of the required particle size in the case of dispersion and by the use of surfactants. The preventions of the action of microorganisms can be brought about by various antibacterial and antifungal agents, for example, parabens, chlorobutanol, phenol, benzyl alcohol, sorbic acid, and the like.

In embodiments, the premix composition can include isotonic agents, for example, sugars or sodium chloride. Prolonged absorption of the injectable compositions can be brought about by the use in the compositions of agents delaying absorption, for example, aluminum monosterate and gelatin. Sterile injectable solutions may be prepared by incorporating the dexmedetomidine in the required amounts in the appropriate solvent with various of the other ingredients enumerated above, as required, followed by filter or terminal sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

In embodiments, the premix formulation may contain an excipient. Pharmaceutically acceptable excipients which may be included in the formulation are buffers such as citrate buffer, phosphate buffer, acetate buffer, and bicarbonate buffer; amino acids; urea; alcohols; ascorbic acid; phospholipids; proteins, such as serum albumin, collagen, and gelatin; salts such as EDTA or EGTA, and sodium chloride; liposomes; polyvinylpyrrolidone; sugars, such as dextran, mannitol, sorbitol, and glycerol; propylene glycol and polyethylene glycol (e.g., PEG-4000, PEG-6000); glycerol; glycine; lipids; preservatives; suspending agents; stabilizers; and dyes. As used herein, the term "stabilizer" refers to a compound optionally used in the pharmaceutical compositions of the present invention in order to avoid the need for sulphite salts and increase storage life. Non-limiting examples of stabilizers include antioxidants. Buffer systems for use with the formulations include citrate; acetate; bicarbonate; and phosphate buffers.

In embodiments, the premix formulation also may contain a non-ionic detergent. Preferred non-ionic detergents include Polysorbate 20, Polysorbate 80, Triton X-100, Triton X-114, Nonidet P-40, Octyl .alpha.-glucoside, Octyl .beta.-glucoside, Brij 35, Pluronic, and Tween 20.

In embodiments, the premix formulations of the present invention can be sterilized. Non-limiting examples of sterilization techniques include filtration through a bacterial-retaining filter, terminal sterilization, incorporation of sterilizing agents, irradiation, and heating.

In embodiments, the premix dexmedetomidine composition of the present invention comprises a pharmaceutically acceptable solvent or carrier system in which an active ingredient is dissolved in said solvent or carrier system. The pharmaceutically acceptable solvent may be an aqueous solvent such as water, physiological saline and buffer, in which the active ingredient is dissolved.

In embodiments, an effective minor amount of at least one buffer component can be incorporated into the composition to stabilize or to maintain the composition at the desired pH. Suitable buffer is selected from but not limited to a group comprising phosphate buffer, acetate buffer, borate buffer, citrate buffer, and the like, and mixtures thereof.

In embodiments, preservatives can be added to the premix composition in order to inhibit the growth of microbial contaminants and suppress biodegradation. Suitable preservative is selected from but not limited to a group comprising benzalkonium chloride, benzethonium chloride, chlorhexidine gluconate, chlorobutanol, benzyl alcohol, sodium dehydroacetate, p-hydroxybenzoate, and the like, and mixtures thereof.

In embodiments, the premix composition can comprise a chelating agent. Suitable chelating agent is selected from but not limited to a group comprising edetic acid, edetic acid salts like disodium edetate, sodium edetate, edetate calcium disodium, trisodium edetate and the like, and mixtures thereof.

In embodiments, the premix compositions of the present invention have a pH of about 3 to about 9, or about 5 to about 7. Suitable pH-adjusting agent that can be used in the premix composition of the present invention is selected from but not limited to a group comprising hydrochloric acid, sodium hydroxide, acetic acid, phosphoric acid, and mixtures thereof.

In embodiments, the process of making premix dexmedetomidine composition of the present invention comprises the following steps:

1. Adding sodium chloride to water for injection (WFI);
2. Adding dexmedetomidine to the above solution;
3. Making the final volume with WFI;
4. Optionally adjusting the pH of solution between 4.5 to 7.0;
5. Filtering the solution;
6. Filling the solution of step (5) into a Polypropylene homopolymer pack and sealing;
7. Optionally Autoclaving the Polypropylene homopolymer pack.

In embodiments, the process of making premix dexmedetomidine composition of the present invention comprises the following steps:
1. Adding sodium chloride to water for injection (WFI);
2. Adding dexmedetomidine to the above solution;
3. Making the final volume with WFI;
4. Adjusting the pH of solution between 5.0 to 6.0;
5. Filtering the solution using 0.22 µm filter;
6. Filling the solution of step (5) into a Polypropylene homopolymer pack and sealing;
7. Autoclaving the Polypropylene homopolymer pack.

In certain embodiments, the stable premix dexmedetomidine composition is disposed within a sealed container.

In certain embodiments, the stable premix dexmedetomidine composition is disposed within a sealed single layer or multilayer film pack, wherein each layer made up of polypropylene homopolymer.

In certain embodiments, the stable premix dexmedetomidine composition is disposed within a sealed container/packaging, which comprises multilayer polypropylene homopolymer coextruded film capable of autoclave sterilization.

In certain embodiments, the premix dexmedetomidine composition is disposed within a sealed container/packaging which comprises multilayer polypropylene homopolymer coextruded film bag.

In certain embodiments, the premix dexmedetomidine composition is disposed in multilayer polypropylene homopolymer coextruded film bag with modified polypropylene Twist off port.

In other non-limiting embodiments, the premix dexmedetomidine compositions of the present invention can be administered as an anxiolytic analgesic to a patient. In certain embodiments, the composition can be administered as a premedication prior to an operation with or without administration of an amount of an anesthetic effective to achieve a desired level of local or general anesthesia.

In other non-limiting embodiments, the dexmedetomidine compositions of the present invention can be administered as a sedative. In certain embodiments, the composition is administered preoperatively to potentiate the effect of an anesthetic, wherein administration of the composition reduces the amount of anesthetic required to achieve a desired level of anesthesia.

In other non-limiting embodiments, the dexmedetomidine compositions of the present invention that is premix ready-to-use formulations in multilayered propylene homopolymer container provides physical and/or chemical stability when stored at 40° C./25% RH for 6 months and at 25° C./40% RH for 12 months.

The following examples are intended to serve as illustrations of the present invention only and do not restrict the scope of the invention in any manner whatsoever.

EXAMPLE 1

The premix formulation according to present invention was prepared as follows.

TABLE 1

Composition of the premix formulations of the present invention

| Sr. No. | Ingredients | Quantity |
|---|---|---|
| 1 | Dexmedetomidine Hydrochloride | 4.8 mcg/mL |
| 2 | Sodium Chloride | 9.0 mg/mL |
| 3 | Water for injection | q.s to 1 mL |

Step-1: Hot water for injection (WFI) was collected and transferred from the preparatory vessel to the SS 316L Makeup vessel such that WFI approximately equivalent to 90% of the batch size remained in the preparatory vessel.

Step-2: To WFI in the preparatory vessel, sodium chloride was added gradually under continuous stirring. The sodium chloride container was rinsed with cooled WFI from Makeup vessel and added to the bulk solution in the preparatory vessel.

Step-3: Dexmedetomidine Hydrochloride was added gradually to step-2 under continuous stirring. The residual drug was rinsed with cooled WFI from Makeup vessel and added to the bulk solution in the preparatory vessel, and stirring continued till clear solution obtained.

Step-4: The weight of solution was made upto 100% of batch size using WFI.

Step-5: pH of the solution was adjusted to 5.5.

Step-6: The Premix formulation was filtered through 0.22 µm filter. Then the filtered solution was filled and sealed respectively into four different multilayered packs:
(i) Three layer pack having crystallizable Polyethylene terephthalate, Polyethylene and modified Propylene Copolymer (cPET/PE/EPC) layer.
(ii) Three layer pack having Polypropylene, Linear Low Density Polyethylene (PP/LLDPE/COP) layer.
(iii) Three layer pack having High Density Polyethylene, Linear Low Density Polyethylene and High Density Polyethylene (HDPE/LLDPE/HDPE) layer
(iv) Three layer pack having Polypropylene homopolymer (PP/PP/PP) layer. Autoclaving at 121° C. for 20 minutes for all 4 sealed packs were done.

Physical and chemical stability of dexmedetomidine premix formulation were evaluated in all 4 multilayered packs at initial state (Unautoclaved) and Autoclaved state at 121° C. for 20 minutes. Assay and RS (Related substances/Impurities) study was conducted on the composition for initial (Unautoclaved) and Autoclaved at 121° C. for 20 minutes. The results are provided in Table-2, Table-3, Table-4 and Table-5.

TABLE 2

Physical stability, pH and Assay study results of premix formulation of example 1 in multilayered bag consisting of three layer having cPET/PE/EPC layer.
The Assay results indicate that there was drop in drug potency at initial state (Unautoclaved) and after autoclaving at 121° C. for 20 minutes. The drug potency value was much more below the specified limits i.e. acceptance criteria. Hence, due to failure in Assay Test, Related substance study was not performed. Based on this stability study, it was concluded that this multilayered pack (cPET/PE/EPC) was not suitable for dexmedetomidine premix formulation.

| | | Volume of Bag | | | |
|---|---|---|---|---|---|
| | | 50 mL Bag | | 100 mL Bag | |
| Test parameters | Tentative Specifications | Unautoclaved | Autoclaved at 121° C. 20 minutes | Unautoclaved | Autoclaved at 121° C. 20 minutes |
| Description | Clear colorless solution | Clear colorless solution | Clear colorless solution | Clear colorless solution | Clear colorless solution |
| pH | 4.5-7.0 | 6.30 | 5.75 | 6.22 | 5.67 |
| Assay (by HPLC, % labeled amount) | 90.0-110.0 | 76.8 | 77.0 | 87.3 | 87.3 |
| Related substances ( % by HPLC) | | | | | |
| Any Individual unspecified Impurity | Not more than 0.5 | Not assessed due to Failure in Assay Test | | | |
| Total Impurities | Not more than 2.0 | Not assessed due to Failure in Assay Test | | | |

TABLE 3

Physical stability, pH, Assay and Related substance study results of premix formulation of example 1 in multilayered bag consisting of three layer having PP/LLDPE/COP layer.
The results of the Related substances indicate that there was impurity formation at initial (Unautoclaved) and after autoclaving at 121° C. for 20 minutes. Significant levels of impurity i.e. detectable amounts is generally not preferred at the initial stage i.e. after compounding premix parenteral formulations. Based on this stability study, it was concluded that this multilayered pack (PP/LLDPE/COP) was not suitable for dexmedetomidine premix formulation.

| | | Volume of Bag | | | |
|---|---|---|---|---|---|
| | | 50 mL Bag | | 100 mL Bag | |
| Test parameters | Tentative Specifications | Unautoclaved | Autoclaved at 121° C. 20 minutes | Unautoclaved | Autoclaved at 121° C. 20 minutes |
| Description | Clear colorless solution | Clear colorless solution | Clear colorless solution | Clear colorless solution | Clear colorless solution |
| pH | 4.5-7.0 | 5.89 | 5.87 | 5.90 | 5.89 |
| Assay (by HPLC, % labeled amount) | 90.0-110.0 | 100.8 | 101.5 | 101 | 101.3 |
| Related substances ( % by HPLC) | | | | | |
| Any Individual unspecified Impurity | Not more than 0.5 | 0.1 | 0.12 | 0.11 | 0.15 |
| Total Impurities | Not more than 2.0 | 0.1 | 0.12 | 0.11 | 0.15 |

TABLE 4

Physical stability, pH, Assay and Related substance study results of premix formulation of example 1 in multilayered bag consisting of three layer having HDPE/LLDPE/HDPE layer.
The results of the Assay indicate that there was drop in drug potency after autoclaving at 121° C. for 20 minutes. The results of the Related substances indicate that there was impurity formation at initial (Unautoclaved) and after autoclaving at 121° C. for 20 minutes. Significant levels of impurity i.e. detectable amounts is generally not preferred at the initial stage i.e. after compounding premix parenteral formulations. Based on this stability study, it was concluded that this multilayered pack (HDPE/LLDPE/HDPE) was not suitable for dexmedetomidine premix formulation.

|  |  | Volume of Bag | | | |
|---|---|---|---|---|---|
|  |  | 50 mL Bag | | 100 mL Bag | |
| Test parameters | Tentative Specifications | Unautoclaved | Autoclaved at 121° C. 20 minutes | Unautoclaved | Autoclaved at 121° C. 20 minutes |
| Description | Clear colorless solution | Clear colorless solution | Clear colorless solution | Clear colorless solution | Clear colorless solution |
| pH | 4.5-7.0 | 5.94 | 5.97 | 5.91 | 5.96 |
| Assay (by HPLC, % labeled amount) | 90.0-110.0 | 101 | 98 | 101 | 97.8 |
| Related substances ( % by HPLC) | | | | | |
| Any Individual unspecified Impurity | Not more than 0.5 | 0.12 | 0.24 | 0.1 | 0.17 |
| Total Impurities | Not more than 2.0 | 0.12 | 0.3 | 0.1 | 0.28 |

TABLE 5

Physical stability, pH, Assay and Related substance study results of premix formulation of example 1 in multilayered bag consisting of three layer having Polypropylene Homopolymer (PP/PP/PP).
Surprisingly, the Assay results indicate that there was no substantial drop in drug potency at initial (Unautoclaved) and after autoclaving at 121° C. for 20 minutes. The drug potency value was well within the specified limits i.e. acceptance criteria. Furthermore, the results of the Related substances indicate that there were no detectable amounts of impurities at initial (Unautoclaved) and after autoclaving at 121° C. for 20 minutes. Also there were no significant changes in pH and description of the product. Based on this stability study, it was concluded that this multilayered pack Polypropylene Homopolymer (PP/PP/PP) was suitable for dexmedetomidine premix formulation.

|  |  | Volume of Bag | | | |
|---|---|---|---|---|---|
|  |  | 50 mL Bag | | 100 mL Bag | |
| Test parameters | Tentative Specifications | Unautoclaved | Autoclaved at 121° C. 20 minutes | Unautoclaved | Autoclaved at 121° C. 20 minutes |
| Description | Clear colorless solution | Clear colorless solution | Clear colorless solution | Clear colorless solution | Clear colorless solution |
| pH | 4.5-7.0 | 6.33 | 6.73 | 6.66 | 6.18 |
| Assay (by HPLC. | 90.0-110.0 | 102.8 | 100.8 | 102.3 | 101.3 |
| Related substances ( % by HPLC) | | | | | |
| Any Individual | Not more than 0.5 | ND | ND | ND | ND |
| Total | Not more | ND | ND | ND | ND |

ND: Not detected

Based on the initial stability study (i.e. Unautoclaved and Autoclaved) it was concluded that multilayered polypropylene homopolymer (PP/PP/PP) pack was most suitable for dexmedetomidine premix formulation. Therefore, stability studies were carried out fordexmedetomidine premix formulations of example 1 in multilayered polypropylene homopolymer (PP/PP/PP) containers.

The stability studies were carried out for Description, pH, Assay & Related substances under the following two conditions and the results were provided below under Table 6, Table 7, Table 8 & Table 9:

(a) 40° C. and 25% relative humidity (RH) over a time period of 6 months.
(b) 25° C./40% RH over a time period of 12 months.

Assay and RS (related substances/impurities) study was conducted on the composition for initial and 6 months samples stored at accelerated conditions. The results are provided in Table-6 and Table-7.

TABLE 6

Physical stability, pH and Assay study results of premix formulation of example 1.
The results of the Assay indicate that there was no substantial drop in drug potency at initial and during the storage period. The drug potency value was well within the specified limits i.e. acceptance criteria. Further, there were no significant changes in pH and description of the product.

| | | | 40° C./25% RH | | | | |
|---|---|---|---|---|---|---|---|
| Test | Specification | Initial | 1M | 2M | 3M | 4.5M | 6M |
| Description | Clear colorless free from visible particles | Clear colorless free from visible particles | | | | | |
| pH | 4.5-7.0 | 5.53 | 5.24 | 4.98 | 4.89 | 4.54 | 4.63 |
| Assay (%) | 90-110 | 97.4 | 97.3 | 95.7 | 99.6 | 96.6 | 95.5 |

TABLE 7

Related substances (RS) study results of premix formulation of example 1. The RS results indicate these were well within the specified limits i.e. acceptance criteria.

| | | | 40° C./25% RH | | | | |
|---|---|---|---|---|---|---|---|
| Test | Specification | Initial | 1M | 2M | 3M | 4.5M | 6M |
| A) Known Impurities | | | | | | | |
| Ketone impurity | 0.5 | ND | ND | ND | ND | ND | ND |
| Ethyl Dexmedetomidine | 0.5 | ND | ND | ND | ND | ND | ND |
| Olefin Impurity | 0.5 | ND | ND | ND | ND | ND | ND |
| B) Maximum Unknown Impurity | NMT 0.50 | 0.08 | 0.14 | 0.06 | 0.02 | 0.07 | 0.1 |
| C) Total impurities | NMT 2.0 | 0.15 | 0.14 | 0.16 | 0.02 | 0.12 | 0.12 |

ND = Not Detected;
NMT = Not More Than

Based on the above studies, it can be concluded that the stability of the drug product was maintained in the multilayered polypropylene homopolymer container/packaging.

Assay and RS (related substances/impurities) study was conducted on the composition for initial and 12 months samples stored at real time stability conditions. The results are provided in Table-8 and Table-9.

TABLE 8

Physical stability, pH and Assay study results of premix formulation of example 1.
The results of the Assay indicate that there was no substantial drop in drug potency at initial and during the storage period. The drug potency values was well within the specified limits i.e. acceptance criteria. Further, there were no significant changes in pH and description of the product.

| | | | 25° C./40% RH | | | |
|---|---|---|---|---|---|---|
| Test | Specification | Initial | 3M | 6M | 9M | 12M |
| Description | Clear colorless free from visible particles | Clear colorless free from visible particles | | | | |
| pH | 4.5-7.0 | 5.53 | 5.38 | 5.65 | 5.56 | 5.60 |
| Assay (%) | 90-110 | 97.4 | 97.6 | 95.3 | 96.6 | 97.3 |

TABLE 9

Related substances (RS) study results of premix formulation of example 1. The RS results indicate these were well within the specified limits i.e. acceptance criteria.

| | | | 25° C./40% RH | | | |
|---|---|---|---|---|---|---|
| Test | Specification | Initial | 3M | 6M | 9M | 12M |
| A) Known Impurities | | | | | | |
| Ketone impurity | 0.5 | ND | ND | ND | ND | ND |
| Ethyl Dexmedetomidine | 0.5 | ND | ND | ND | ND | ND |
| Olefin Impurity | 0.5 | ND | ND | ND | ND | ND |
| B) Maximum Unknown Impurity | NMT 0.50 | 0.08 | 0.04 | 0.02 | 0.01 | ND |
| C) Total impurities | NMT 2.0 | 0.15 | 0.09 | 0.02 | 0.01 | ND |

ND = Not Detected;
NMT = Not More Than

Based on the above studies, it can be concluded that the stability of the drug product was maintained in the multilayered polypropylene homopolymer container/packaging.

We claim:

1. A stable premix composition comprising dexmedetomidine or a pharmaceutically acceptable salt thereof, in a multilayered film pack, wherein the premix composition wetted layer of the multilayered film pack is a polypropylene homopolymer.

2. The stable premix composition of claim 1 comprising 4 mcg/mL of dexmedetomidine or a pharmaceutically acceptable salt thereof, 9 mg/mL of sodium chloride and water.

3. The stable premix composition of claim 1 wherein the pack is a film bag.

4. The stable premix composition of claim 1 which is in the form of a ready-to-use preparation.

5. The stable premix composition of claim 1 having a total volume selected from 20 mL, 50 mL and 100 mL.

6. The polypropylene film bag of claim 1 comprising at least one injection port, one tube port and one twist off port.

7. The stable premix composition of claim 1 wherein dexmedetomidine or a pharmaceutically acceptable salt thereof is present in a concentration of about 0.05 μg/ml to about 15 μg/ml.

8. A process for preparation of stable premix composition of claim 1 comprising:
i) Adding sodium chloride to water;
ii) Adding dexmedetomidine to the step (i) solution;
iii) Making the final volume with water;

iv) Adjusting the pH between 4.5 to 7.0;
v) Filtering the solution of step (iv);
vi) Filling the solution into multilayered film pack wherein the formulation-wetted layer in the multilayered film is made from polypropylene homopolymer and sealing the pack;
vii) Autoclaving the solution of step (vi).

9. The stable premix composition of claim 1 used for sedating initially intubated and mechanically ventilated patients during treatment in an intensive care setting, and for sedating of non-intubated patients prior to and/or during surgical and other procedures.

* * * * *